US005736527A

United States Patent [19]
Malley et al.

[11] Patent Number: 5,736,527
[45] Date of Patent: *Apr. 7, 1998

[54] METHOD OF TREATING HIV IN HUMANS BY ADMINISTRATION OF DDI AND HYDROXYCARBAMIDE

[75] Inventors: Serge D. Malley, Villeurbanne; Jorge R. Vila, Lyon, both of France

[73] Assignee: Compagnie de Developpment Aguettant S.A., Lyon, France

[*] Notice: The term of this patent shall not extend beyond the expiration date of Pat. No. 5,521,161.

[21] Appl. No.: 617,421

[22] Filed: Mar. 18, 1996

Related U.S. Application Data

[63] Continuation of Ser. No. 169,253, Dec. 20, 1993, Pat. No. 5,521,161.
[51] Int. Cl.$^6$ ...................................................... A61K 31/70
[52] U.S. Cl. .......................... 514/45; 514/579; 514/588; 536/27.14; 536/27.8
[58] Field of Search ............................... 514/579, 45, 46, 514/588; 536/27.14, 27.8

[56] References Cited

U.S. PATENT DOCUMENTS

| | | | |
|---|---|---|---|
| 4,708,818 | 11/1987 | Montagnier et al. | 435/5 |
| 5,026,687 | 6/1991 | Yarchoan et al. | 514/45 |
| 5,110,600 | 5/1992 | Green | 424/45 D |
| 5,300,059 | 4/1994 | Rubinstein et al. | 604/408 |
| 5,521,161 | 5/1996 | Malley et al. | 514/45 |

FOREIGN PATENT DOCUMENTS

| | | |
|---|---|---|
| 0 206 497 | 12/1986 | European Pat. Off. . |
| WO 87/01284 | 3/1987 | WIPO . |
| WO 94/27590 | 12/1994 | WIPO . |

OTHER PUBLICATIONS

*Low levels of deoxynucleotides in peripheral blood lymphocytes: A strategy to inhibit human immunodeficiency virus type 1 replication*, by Gao et al.; Proc. Natl. Acad. Sci., USA, vol. 90, pp. 8925–8928, Oct. 1993 Medical Sciences.

*Hydroxyurea as an Inhibitor of Human Immunodeficiency Virus–Type 1 Replication*, by Franco Lori, et al. Science, vol. 266:801–805, Nov., 1994.

*The Anti–HTLV–III (Anti–HIV) and Cytotoxic Activity of 2',3'–Didehydro–2'3'–dideoxyribonucleosides: A Comparison with Their Parental 2',3'–Dideoxyribonucleosides* by Jan Balzarini et al., Molecular Pharmacology, 32:162–167 (1987).

*AIDS Is More Than HIV: Part I*, by Robert S. Root–Bernstein, Ph.D., Genetic Engineering News pp. 4–6, Sep., 1992.

*AIDS Is More Than HIV: Part II*, by Robert S. Root–Bernstein, Ph.D., Genetic Engineering News pp. 4–5, Sep., 1992.

*Effects of Hydroxyurea and Thymidine Derivatives on the Uptake and Metabolism of Deoxycytidine and Arabinofuranosylcytosine in Log Phase and Contact–Inhibited Human Diploid Fibroblasts* by D. Snyder et al., Molecular Pharmacology, 28:574–580 (1985).

*Prevention of activation of HIV–1 by antiviral agents in OM–10.1 cells*, by P. M. Feorino et al., Antiviral Chemistry & Chemotherapy (1993) 4(1), 55–63.

*Inhibition Of Polymerases –$\alpha$And $\beta$Completely Blocks DNA Repair Induced By UV Irradiation In Cultured Mouse Neronal Cells*, by Federico Licastro et al., Biochemical and Biophysical Research Communications, pp. 929–933, v. 132(3), 1985.

*Cellular Pharmacology and Anti–HIV Activity of 2',3'–Dideoxyguanosine* by M.E. Busso et al., Aids Research and Human Retroviruses, vol. 6, Nov., 1990, pp. 1139–1146.

*Acid–Stable 2'–Fluoro Purine Dideoxynucleosides as Active Agents against HIV*, by Victor E. Marquez et al., J. Med. Cm. 1990, 33, pp. 978–985.

*The Human Immunodeficiency Virus: Infectivity and Mechanisms of Pathogenes*, by Anthony S. Fauci, National Institute of Allergy and Infectious Diseases, National Institutes of Health, Science vol. 239, Feb., 1988, pp. 617–622.

*Kaposi's Sarcoma and Pheumocystis Pneumonia Among Homosexual Men—New York City and California*, Center For Disease Control, Morbidity and Mortality Weekly Report, U.S. Dept. of Health and Human Services; Jul. 3, 1981/vol. 30/No. 25. pp. 305–308.

*Suppression of HIV production in resting lymphocytes by combining didanosine and hydroxamate compounds*, by Serge D. Malley et al., The Lancet (Reprinted from The Lancet Saturday 21 May 1994) vol. 343 No. 9808 p. 1292.

*Quiescent T Lymphocytes as an Inducible Virus Reservoir in HIV–1 Infection*, by Bukrinsky et al., Science, vol. 254, Mar. 1991, pp. 423–427.

*The Reservoir for HIV–1 in Human Peripheral Blood Is a T Cell That Maintains Expression of CD4*, by Steven M. Schnittman et al., Science, vol. 245, Jan., 1989, pp. 305–308.

*Lymphoid Germinal Centers Are Reservoirs of Human Immunodeficienctcy Virus Type 1 RNA*, by Cecil H. Fox et al., Journal of Infections Diseases 1991:164; 1051–1057.

*The accumulation of DNA breaks due to incision; comparative studies with various inhibitors*, Snyder et al., IRL Press Limited, Oxf, England, 13–33.

*Multifactorial Nature of Human Immunodeficiency Virus Disease: Implications for Therapy*, by Anthony S. Fauci, Science vol. 262, , Nov., 1993, pp. 1011–1018.

*HIV–1 Entry into Quiescent Primary Lymphocytes: Molecular Analysis Reveals a Labile, Latent Viral Structure*, by Jerome A. Zack et al., Cell, vol. 61, 213–222, Apr., 1990.

*Therapy For Human Immunodeficiency Virus Infection*, by Martin S. Hirsch et al., The New England Journal of Medicine, Jun., 1993, vol. 329, No. 23, pp. 1686–1696.

(List continued on next page.)

Primary Examiner—John Kight
Assistant Examiner—L. Eric Crane
Attorney, Agent, or Firm—Bell, Boyd & Lloyd

[57] ABSTRACT

A method and composition for inhibiting the spread of a retrovirus such as HIV in a human cell population in which a retrovirus such as HIV is present has been found. The spread of the retrovirus is inhibited by treatment of the cells with a synergistic combination mixture of a dideoxyribonucleoside excluding AZT and hydroxycarbamide.

3 Claims, 3 Drawing Sheets

OTHER PUBLICATIONS

*Rapid and automated tetrazolium–based colorimetric assay for the detection of anti–HIV compounds*, by Rudi Pauwels et al., Journal of Virological Methods, 20 (1988) 309–321.

*Clinical Pharmacology Of 3'–Azido–2', 3'–Dideoxythymidine (Zidovudine) And Related Dideoxynucleosides*, by Robert Yarchoan et al., The New England Journal of Medicine, vol. 321, No. 11, pp. 726–738 (1989).

*Use of evolutionary limitations of HIV–1 multidrug resistance to optimize therapy*, by Yung–Kang Chow et al., Nature, 361, 650–654 (18 Feb. 1993).

*Hydroxyurea increases the phosphorylation of 3'–fluorothymidine and 3'–zidothymidine in CEM cells*, by Anna Karlsson et al., Eur J. Biochem. 186, 689–694 (1989).

Meyerhans et al., "The Intracellular Nucleotide Pool Effects HIV Replication", VIII International Conference on AIDS/III STD World Congress, vol. 2, Jul. 1992, pp. A22–2118.

T'Ang et al., "Optimization of the Schiff Bases of N–Hydroxy–N'aminoguanidine as Anticancer and Antiviral Agents", J. Med. Chem., vol. 28, 1985, pp. 1103–1106.

Lien, "Ribonucleotide reductase inhibitors as anticancer and antiviral agents", Progress in Drug Research, vol. 31, 1987, pp. 101–126.

Lori et al., "Hydroxyurea Inhibits HIV–1 Replication by AP Inducing Low dNTP Levels. A Cellular Enzyme as a Target to Inhibit HIV–1", Antiviral Res., vol. 23/Sup. 1, 1994, p. 63.

Gao et al., "Anti–HIV–1 Activity of Hydroxyurea in Combination with 2',3'–dideoxynucleosides", Clinical Research, vol. 42, No. 2, 1994, p. 280A.

Matsumoto et al., "Inhibition of RNA Synthesis by Deoxyadenosine Plus Deoxycoformycin in Resting Lymphocytes", The Journal of Immunology, vol.131, 1983, pp. 2762–2766.

Gao et al., "Low levels of deoxynucleotides in peripheral blood lymphocytes: A strategy to inhibit human immuno-deficiency virus type 1 replication", Proc. Natl. Acad. Sci. USA, vol. 90, Oct. 1993, pp. 8925–8928.

Fischl, "Treatment of HIV Disease in 1993/1994", AIDS Clin. Rev., vol. 94, 1993, pp. 167–187.

International Search Report for Internation Application No. PCT/US 94/05515.

Balzarini et al., "2', 3'–Dideoxycytidine: Regulation of its Metabolism and Anti–retroviral Potency by Natural Pyrimidine Nucleosides and by Inhibitors of Pyrimidine Nucleotide Synthesis", Molecular Pharmacology, vol. 32, 1987, pp. 798–806.

Safrin et al., "Potential for Combined Therapy with 348U87, a Ribonucleotide Reductase Inhibitor, and Acyclovir as Treatment for Acyclovir–Resistant Herpes Simplex Virus Infection", Journal of Medical Virology Supplement 1, 1993, pp. 146–149.

Wilson et al., "Purinogenic Immunodeficiency Diseases—Differential Effects of Deoxyadenosine and Deoxyguanosine on DNA Synthesis in Human T Lymphoblasts", J. Clin. Invest., vol. 64, 1979, pp. 1475–1484.

Albert et al., "Deoxyadenosine Toxicity and Cell Cycle Arrest in Hydroxyurea–Resistant S49 T–Lymphoma Cells", Experimental Cell Research, vol. 179, 1988, pp. 417–428.

*Ganciclovir Antagonizes the Anit–Human Immunodeficiency Virus Type 1 Activity of Zidovudine and Didanosine In Vitro*, by Media et al.; Antimicrobial Agents and Chemotherapy, May 1992, pp. 1127–1130, vol. 36, No. 5.

*Synergistic anti–human immunodeficiency virus type 1 effect of hydroxamate compounds with 2', 3'–dideoxyinosine in infected resting human lymphocytes*, by Malley et al., Proc. Natl. Acad. Sci USA vol. 91, pp. 11017–11021, Nov. 1994, Medical Sciences.

Perno et al., "Inhibition of Human Immunodeficiency Virus AY (HIV–1/HTLV–III$_{Ba-L}$) Replication in Fresh and Cultured Human Peripheral Blood Monocytes/Macrophages by Azidothymidine and Related 2',3'–Dideoxynucleosides", J. of Exp. Medicine, vol. 168, 1988, pp. 1111–1125.

Biron et al., "Anti–HIV Activity of the Combination of Didanosine and Hydroxyurea in HIV–1–Infected Individuals," J. Acquired Immune Deficiency Syndromes and Human Retrovirology, 10, 36–40 (1995).

Barre–Sinoussi et al., "Isolation of a T–Lymphotropic Retrovirus from a Patient at Risk for Acquired Immune Deficiency Syndrome (AIDS)," Science, 220, 868–871 (1983).

Snyder et al. (II), "The Accumulation of DNA Breaks Due to Incision; Comparative Studies with Various Inhibitors," Ch. 2 in *DNA Repair and Its Inhibition, Nucleic Acids Symposium Series* No. 13, Collins et al. eds., IRL Press, Oxford, England, 1984, pp. 13–33.

Hao et al., "Factors Determining the Activity of 2', 3'–Dideoxynucleosides in Suppressing Human Immunodeficiency Virus In Vitro," *Molecular Pharmacology*, 34, 431–435 (1988).

Simonelli et al., "Hydroxyurea as an Antiretroviral Drug in HIV Infected Patients: Clinical, Immunological, and Virological Evaluation," Abstract No. 84 in *Book of Abstracts, The Fifth European Conference on Clinical Aspects and Treatment of HIV Infection*, Europoean AIDS Clinical Soc. (Publ.), Copenhagen, Denmark, Sep. 1995.

METHOD OF TREATING HIV IN HUMANS BY ADMINISTRATION OF DDI AND HYDROXYCARBAMIDE

This is a continuation of application Ser. No. 08/169,253, filed Dec. 20, 1993, now U.S. Pat. No. 5,521,161.

FIELD OF THE INVENTION

The present invention relates to a combination of a reverse transcriptase inhibitor and hydroxycarbamide in a synergistically effective amount wherein the combination is useful in inhibiting retroviral spread.

BACKGROUND OF THE INVENTION

The expression "Acquired Immuno-Deficiency Syndrome" (AIDS) was first used in 1981 to describe a state of cellular immune deficiency in homosexuals, characterized by the appearance of opportunistic infections and Kaposi's Sarcoma evolving very aggressively (CDC (Center for Disease Control), MMWR, 30: 305–308.DC, (1981)). In 1983 a retrovirus since called HIV (Human Immunodeficiency Virus type 1) was isolated among AIDS patients (Barré-Sinoussi F. et al Science, 220: 868–870 (1983)).

Over the past several years, researchers and clinicians have gained considerable experience in studying and caring for individuals infected with HIV throughout the often prolonged course of HIV disease and AIDS. On the basis of this experience, it has become clear that the pathogenic mechanisms underlying HIV infection and disease are not unidimensional, but rather are extremely complex (Fauci AS., Science, 239, 617.(1988)). Any attempt to design a comprehensive therapeutic strategy for HIV disease must take this fact into account. (Fauci, 1993, Science, 262:1011–1018).

After entry of the HIV virus into cells and uncoating of the HIV particle, reverse transcription of the viral RNA genome into DNA replicas occurs. Among several forms of unintegrated viral DNA (now containing the long repeats [LTRs], at both the 5' and 3' ends), only the two LTR linear forms can integrate into the host genome. Such a process appears strictly dependent upon cell activation/replication of T lymphocytes, although "resting" T cells are clearly susceptible to HIV infection. (Zack J. A. et al. Cell; 61, 213–222, (1990)). Furthermore, part of the reverse transcription process also can occur in unactivated T cells, a process that results in the accumulation of incomplete DNA molecules, which may persist for several hours and remain capable of being integrated into the host genome if the cell undergoes sufficient activation (Zack J. A. et al, Cell; 61, 213–222 (1990)). Therefore, infected "resting" CD4$^+$T lymphocytes can be considered a transient viral reservoir in infected individuals (Bokrinsky M. I. et al; Science, 254, 423–427, (1991)). These observations are of particular importance in anatomic compartments such as the peripheral blood and lymphoid organs, where the CD4$^+$T cell subset represents the predominant infected cell type (Schmittman S M. et al, Science, 245,305–308, (1989)); (Fox CH. et al J. Infect Dis; 164, 1051–1057, (1991)).

The above discussion provides a sound scientific basis for blocking the initial burst of virus replication and dissemination as well as the persistent replication throughout the course of disease by treating HIV-infected individuals with antiretroviral agents from the earliest time that HIV infection is recognized through the entire course of infection. Unfortunately, currently available agents are only partially effective in suppressing virus replication and spread, and this effect is transient (Hirsch MS, et al, New Engl. J. Med. 328 1686, (1993)). Clear cut, but limited, benefit is seen when 3'-azido-2',3'-dideoxythymidine or azidothymidine (AZT) is given to a patient with advanced HIV disease, and the benefits of early intervention are usually only temporary and do not result in significant long-term advantages with regard to the course of disease and death. (Fauci, 1993, Science, 262:1011–1018).

A number of 2'-3'-dideoxynucleosides have been found to be useful for the treatment or prophylaxis of retroviral infections and especially HIV and AIDS. Examples of such materials include: 2',3'-dideoxy-cytosine (ddC); 2',3'-dideoxy-adenosine (ddA); 2',3'-dideoxy-guanosine (ddG); and 2',3'-dideoxy-inosine (ddI) and 2',3' dideoxy-thymidine (ddT). See European patent application 0206497 and published PCT application number WO 87/01284.

Hydroxycarbamide (HC) was initially synthesized over 120 years ago and has been found to demonstrate activity against a broad spectrum of tumors. (Donehower, Seminars in Onocology, Vol. 19, No. 3, Suppl. 9 (June) 1992: pp 11–19). Additionally, hydroxycarbamide has been used as a viricide. In published PCT application number WO 93/09718, hydroxycarbamide is taught to be useful in a hydrogel polymer coating of a blood bag in order to inhibit viral and HIV infectivity.

Gao et al (PNAS, U.S.A., Vol. 90, pp. 8925–8928, October 1993) disclose that hydroxyurea (hydroxycarbamide) treatment of peripheral blood lymphocytes (PBLs) decreases dNTP levels and the DNA synthesis rate to levels comparable to quiescent PBLs. The article alleges a possible use of hydroxyurea in AIDS therapy.

However, there still remains a need for more effective treatments for the suppression of retroviruses and, in particular, the prevention and/or inhibition of HIV and viral spread. By viral spread, it is intended to include the inhibition of viral replication, and also may include the ability of inhibiting the virus to infect a further host cells.

Objectives of the present invention in the search for new antiretroviral agents include:

1) the identification of compounds with less toxicity and antiviral activity greater than AZT.

2) the development of drug combinations which provide an additive or synergistic effect and decrease the probability of drug resistant isolates.

BRIEF SUMMARY OF THE INVENTION

The present invention relates to a combination of a reverse transcriptase inhibitor and hydroxycarbamide in a synergistic combination wherein the synergistic combination is capable of preventing and/or inhibiting the spread of retroviruses including HIV. More specifically, the present invention relates to a method of preventing and/or inhibiting the spread of retroviruses, including HIV (HIV-1 and HIV-2), HTLV-1, HTLV-2, SIV or HSV, by exposing a cell population, including cells infected by a retrovirus such as, for example, HIV, to a synergistic combination of a reverse transcriptase inhibitor and hydroxycarbamide. Additionally, the present invention encompasses the treatment of HIV-infected and AIDS patients with a synergistic combination of a reverse transcriptase inhibitor and hydroxycarbamide in order to prevent and/or inhibit the spread of HIV in these patients.

In a preferred embodiment of the present invention, the reverse transcriptase inhibitors include dideoxynucleosides, such as, for example, ddI, ddA, ddG and ddT (DT4).

In particular and in the preferred combination of the present invention, it has been found that a synergistic combination of hydroxycarbamide (HC) and 2',3'-dideoxyinosine (ddI) can be formed which is especially effective in preventing and/or inhibiting HIV spread. The preferred embodiment of the invention encompasses a composition including a pharmaceutical composition comprising a synergistic combination of ddI and HC. The pharmaceutical composition can optionally contain a pharmaceutically acceptable carrier and/or excipient and/or vehicle. The preferred method of the instant invention comprises preventing and/or inhibiting retroviral or HIV spread by treating a cell population, including cells infected with HIV, with a synergistic combination of ddI and HC. Additionally, the preferred method comprises treating an HIV infected or AIDS patient with a synergistic combination of ddI and HC so as to prevent and/or inhibit HIV spread in the patient.

DETAILED DESCRIPTION OF THE INVENTION

The following examples of specific embodiments of the present invention are offered for illustrative purposes only and are not limiting with respect to the scope of the disclosure or claim coverage.

Testing of the mixture of dideoxyinosine (ddI) and hydroxycarbamide (HC) on the spread of the HIV virus was conducted under two types of conditions:

a) CD4+ lymphocytes purified from PBMC, and infected with HIV virus without prior activation/proliferation of these cells by phytohemagglutinin (PHA) and interleukin-2 (IL-2).

b) PBMC preactivated by PHA and IL-2, then infected with the HIV virus.

EXAMPLE 1

The activity of the mixture of ddI and HC on non-activated CD4$^+$ lymphocytes, infected with HIV virus was studied.

Non-activated CD4$^+$ cells were infected, then treated for 7 days by HC, ddI or the combination of the two, then activated by PHA and IL-2 (PHA-IL-2).

Cellular viability between 90% and 100% was observed during the first seven days after infection, both for the infected control and for the infected cells treated with the two drugs separately or in combination. Comparable proliferative cellular response was observed in the presence of PHA-IL-2 for the first 3 days (days 7-9) both in the six virus infected groups and in the non-infected, non-treated donor CD-4$^+$ cells. This proliferative response is associated with cytopathic effect in the infected control group, and in the groups treated with HC alone at 0.05 and 0.15 mM: these groups had greater than 50% loss of viability compared to the uninfected control group; this effect is due to viral replication and is accompanied by large-scale production of p24-HIV in the culture supernatant seen at day 15 (86215 pg of p24/ml for the infected control, 75470 and 82005 for 0.05 and 0.15 mM HC treatment groups, respectively) see FIG. 1.

The cytopathic effect was observed later for the cells treated with 5 μM ddI and reached substantially the same level of p24 production as the infected control 10 days later at day 25 (101080 pg p24/ml), see FIG. 1.

Figure 1:
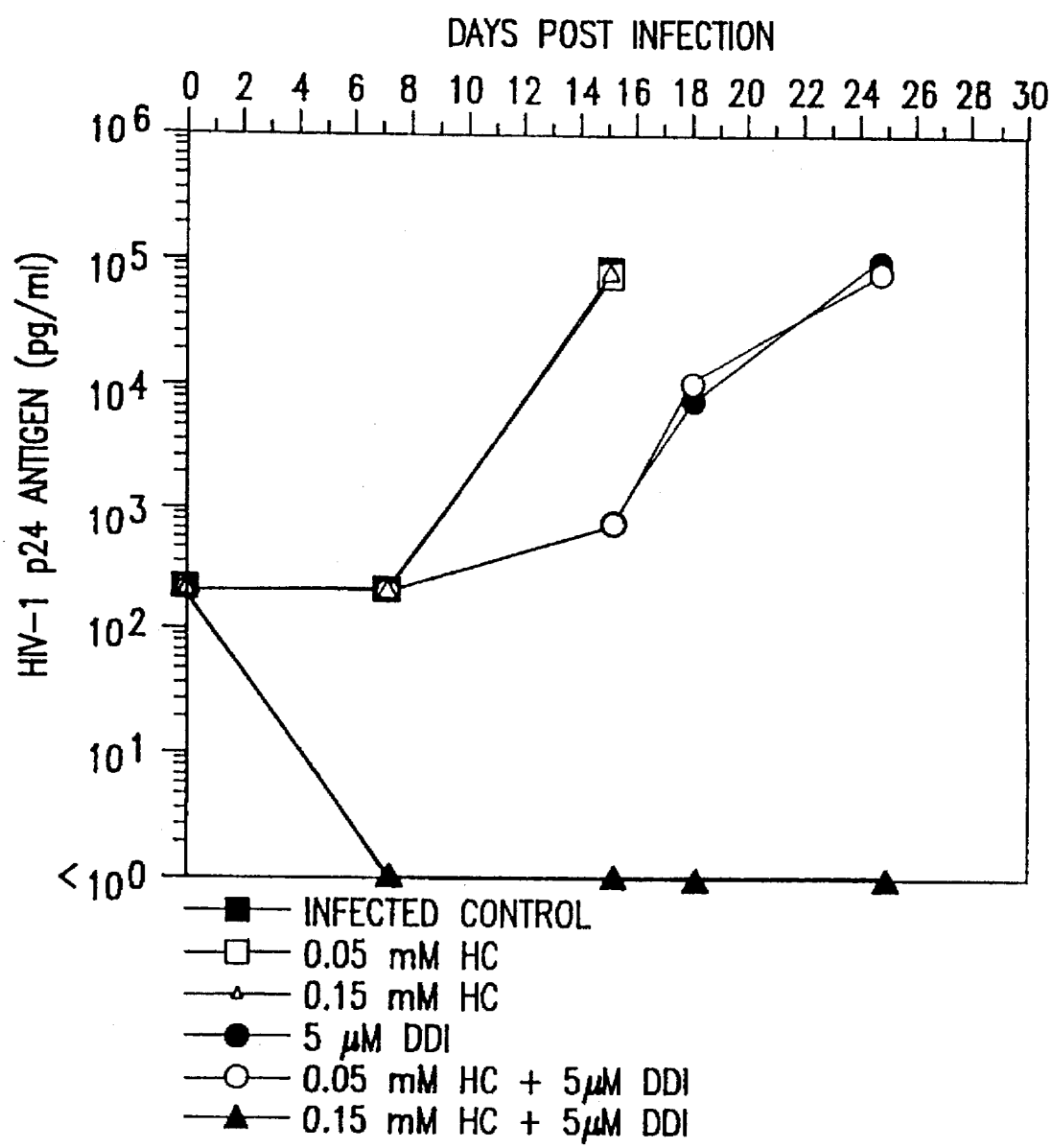
FIG. 1 is a study of the anti-viral activity of a mixture of ddI and HC on non-activated CD4+ lymphocytes infected with the HIV virus.

The mixture of HC at 0.05 mM with ddI at 5 μM does not substantially change the viral replication profile as compared to ddI alone (84883 pg p24/ml at day 25), see FIG. 1.

By contrast, a surprising synergistic effect is observed with the combination 0.15 mM of HC and 5 μM of ddI, where no residual viral production is detectable (<1 pg p24ml) at day 7 and day 25 despite cellular proliferation which is identical to the non-treated, non-infected control (>90% cell viability measured by MTT test).

FIG. 1, in particular, shows a study to the activity of a mixture of ddI and HC on non-activated CD4$^+$ lymphocytes infected with the HIV virus. The CD4$^+$ lymphocytes were purified from PBMC with immunomagnetic beads (Dynabeads® M450). These cells were infected with the HIV-1 virus strain IIIB at a multiplicity of infection of 5 000 tissue culture infectious dose (TCID) per 10$^6$ cells (241 pg/ml p24 antigen equivalent of virus). After 2 hours of virus cell contact, the cells were washed twice and placed in the culture medium RPMI 1640 (supplemented with 10% fetal calf serum (FCS), 2 mM glutamine, penicillin 100 IU/ml and Streptomycin 100 μg/ml) at a density of 1.3×10$^6$ cells/ml. ddI was immediately added at a concentration of 5 μM and HC at concentrations of 0.05 mM and 0.15 mM. The drugs and culture medium were partially renewed (50%) on day 4, maintaining the same concentration of each. On day 7, in order to remove the drugs, the cells were washed twice and put back in culture in the presence of PHA at a concentration of 1 μg/ml and recombinant IL-2 at a concentration of 20 U/ml. This culture was maintained until day 25, with partial renewal (50%) of the medium twice a week. The number of viable cells was quantified by a tetrazolium-based colorimetric 3-(4,5-dimethylthiazol-2-yl)-2,5-diphenyltetrazolium bromide (MTT) method (Pauwels, R. et al *J. Virol. Methods*, 20, 309–321, (1988)), and activity is expressed as a percentage of the signal in the drug-free and virus-free control. Viral replication was quantified by measuring the HIV-1 p24 antigen by ELISA using the Dupont de Nemours kit.

EXAMPLE 2

In order to determine whether or not this synergistic effect of ddI in a mixture with HC is specific to ddI, or whether a similar effect could be observed with AZT, a parallel study was conducted combining HC with azidothymidine (AZT) with surprising results.

Figure 2:
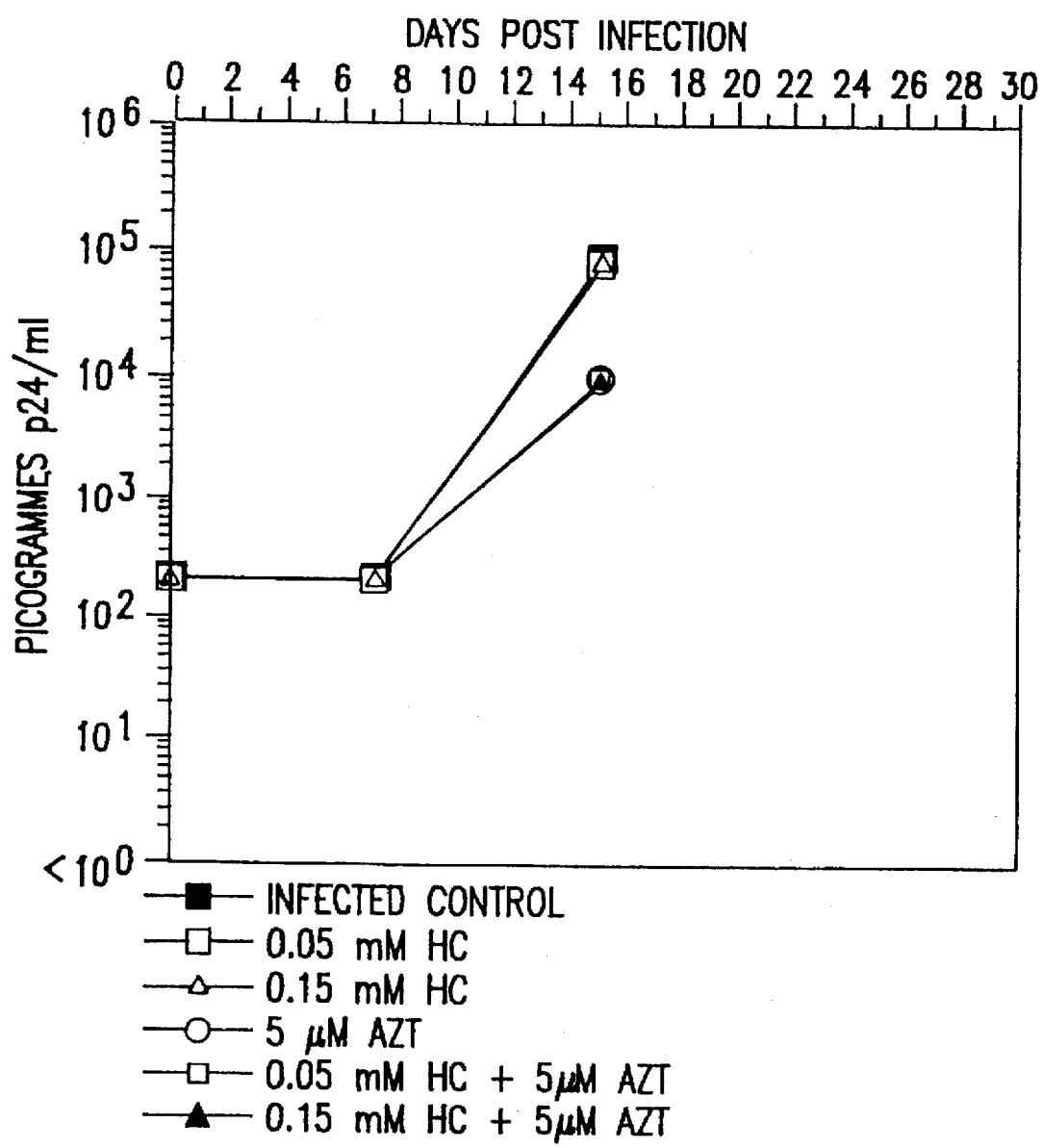
FIG. 2 is a study of the antiviral activity of a mixture of AZT and HC.

As can be seen in FIG. 2, AZT alone at 5 μm has only slight antiviral activity, less than 1 log, (88.4%) inhibition (10030 pg p24/ml compared to 86215 pg p24/ml for infected control), less than ddI at the same dose under the same conditions: 99.1% inhibition (766 pg p24/ml compared to 86215 pg p24/ml for infected control, see FIG. 1). The drug concentration used here are easily attainable in plasma (plasma concentration achievable under treatment conditions: 4 μM for AZT and 10 μM for ddI (Yarchoan et al, *New Engl. J. Med.* 321 726–738,(1989)).

Comparable proliferative cellular response was observed after stimulation by PHA-IL-2 in all groups. This proliferative response is associated with cytopathic effect in the infected control group, and in the groups treated with HC alone at doses of 0.05 and 0.15 mM and combined with AZT at 5 µM (these groups had greater than 50% loss of viability compared to the uninfected control group). The combination of HC at 0.05 mM and at 0.15 mM with AZT at 5 µM (10108 and 9166 pg p24/ml, respectively) does not modify the viral replication profile compared to AZT alone (FIG. 2).

The results show that the synergistic effect which eradicates HIV replication in CD4$^+$ cells non-activated by PHA-IL-2 (Example 1) is not found from the mixture of HC with AZT.

In FIG. 2, there is shown a study of the activity of the combination of AZT and HC on non-activated CD4$^+$ lymphocytes infected with the HIV virus. The CD4$^+$ lymphocytes were purified from PBMC with immunomagnetic beads (Dynabeads® M450). These cells were infected with the HIV-1 virus strain IIIB at a multiplicity of infection of 5 000 tissue culture infectious dose (TCID) per $10^6$ (241 pg/ml p24 antigen equivalent of virus). After 2 hours of virus-cell contact, the cells were washed twice and placed in the culture medium RPMI 1640 (supplemented with 10% FCS, 2 mM glutamine, penicillin 100 IU/ml and streptomycin 100 µg/ml) at a density of $1.3 \times 10^6$ cells/ml. AZT was immediately added at a concentration of 5 µM and HC at a concentration of 0.05 mM and 0.15 mM. The drugs and culture medium were partially renewed (50%) on day 4, maintaining the same concentration of each. On day 7, in order to remove the drugs, the cells were washed twice and put back in culture in the presence of PHA at a concentration of 1 µg/ml and recombinant IL-2 at a concentration of 20 U/ml. This culture was maintained until day 25, with partial renewal (50%) of the medium twice a week. The number of viable cells was quantified by a tetrazolium-based colorimetric 3-(4,5-dimethylthiazol-2-yl)-2,5-diphenyltetrazolium bromide (MTT) method (Pauwels, R. et al *J. Virol. Methods*, 20.309–321, (1988)), and activity is expressed as a percentage of the signal in the drug-free and virus-free control. Viral replication was quantified by measuring the HIV-1 p24 antigen by ELISA using the Dupont de Nemours kit.

EXAMPLE 3

A further study demonstrated inhibition of viral spread in preactivated PBMC culture infected with the HIV virus, by the mixture of HC and ddI.

PBMC preactivated with PHA and IL-2, were infected and treated by HC at 0.15 mM; this concentration corresponds to the $IC_{50}$ (inhibitory concentration 50%) after 3 days measured by MTT tests, with cellular viability >90% (this cell viability was determined by treating the cells with 2% Trypan Blue for 2 min and monitoring for dye exclusion). The combination of 0.15 mM of HC and 10 µM of ddI does not modify the $IC_{50}$ and cellular viability.

As can be seen (FIG. 3), the virus replicated rapidly in the non-treated culture maintaining a stable level as from day 6 (day 6=71815; day 12=72750; day 20=62750 pg p24/ml). Treatment with ddI alone at 10 µM and HC alone at 0.15 mM induces inhibition of 97.1% (2071 pg p24/ml) and 82.6% (12500 pg p24/ml) respectively at day 6. By contrast, a major synergistic effect is observed with the combination of 10 µM ddI and 0.15 mM HC, with an inhibition of 99.8% (100 pg p24/ml) at day 6 and no residual viral production detectable (<1 pg. p24/ml) at day 12 and day 20.

This major synergistic effect, having been demonstrated with non-activated lymphocytes, where the combination of ddI with HC eradicates the HIV infection from the cells, is also observed here where lymphocytes are preactivated and treated with the combination of ddI and HC while the PBMC are replicating.

Figure 3:
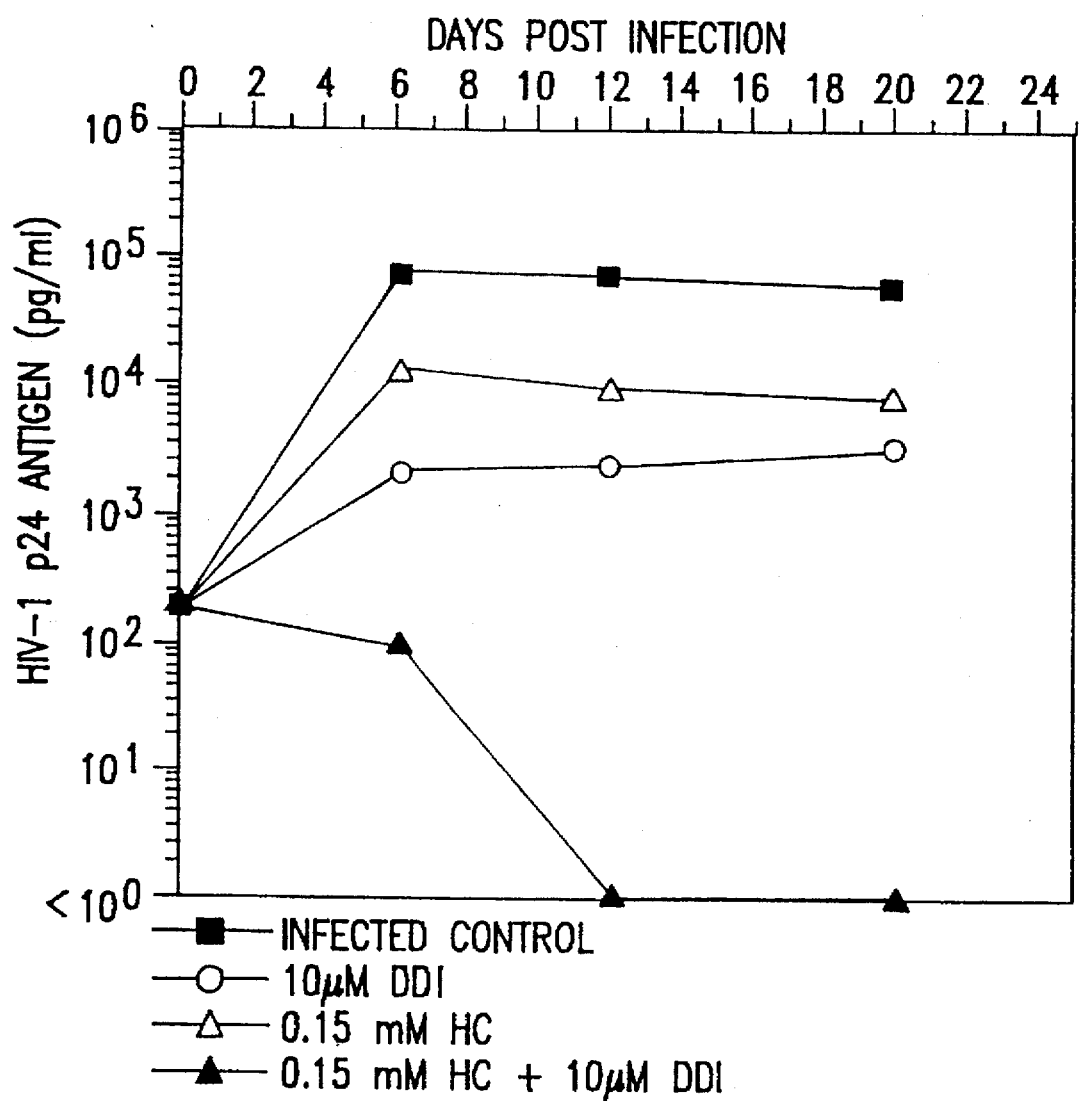
FIG. 3 illustrates the inhibition of viral spread by the mixture of HC and ddI in pre-activated peripheral blood mononuclear cells (PBMC) culture infected with the HIV virus.

In FIG. 3, there is shown the elimination of viral replication by the combination of HC and ddI preactivated PBMC culture infected with the HIV virus. The PBMC were purified from peripheral blood by discontinuous Ficoll density gradient centrifugation. The cells were grown at a density of $1.3 \times 10^6$ cells/ml in RPMI 1640 medium supplemented with 10% FCS, 2 mM glutamine, penicillin 100 IU/ml and streptomycin 100 µg/ml, in the presence of PHA at a concentration of 1 µg/ml and recombinant IL-2 at 20 U/ml for 72 hours, then infected by HIV-1 strain IIIB at a multiplicity of 5000 TCID for $10^6$ cells (241 pg/ml p24 antigen equivalent of virus). In FIG. 3, the first time point represents viral infection of the cells. After 2 hours of virus-cell contact, the cells were washed twice and placed in the culture medium containing IL-2 but without PHA in the presence of ddI at a concentration of 10 µM and of HC at a concentration of 0.15 mM. These cultures were maintained for 20 days, with partial renewal of the medium and of the two drugs twice a week maintaining the initial concentration. At day 6 and day 14 fresh uninfected donor PBMC were added ($5 \times 10^5$/ml) to replenish aged cultures (*Nature*, 361:1993, 650–654). The number of viable cells were quantified by a tetrazolium-based colorimetric 3-(4,5-dimethylthiazol-2-yl)-2,5-diphenyltetrazolium bromide (MTT) method (Pauwels, R. et al *J. Virol. Methods*, 20:309–321, (1988)), and activity is expressed as a percentage of the signal in the drug-free and virus-free control. Viral replication was quantified by measuring the HIV-1 p24 antigen by ELISA using the Dupont de Nemours kit.

Gao et al in *Proc. Nat'l. Acad, Sci. U.S.A.*, cited supra, teach that "human immunodeficiency virus type 1 (HIV-1) viral DNA synthesis in quiescent and activated peripheral blood lymphocytes (PBLs) was studied. Incomplete viral DNA (previously demonstrated to be associated with HIV-1 virions) is carried by HIV-1 virions into quiescent and activated PBLs, contributing to the formation of an early viral DNA pool in these cells. The viral DNA is subsequently completed but only extremely slowly and inefficiently in quiescent PBLs compared to that in stimulated PBLs. We find that this correlates with significantly lower levels of dNTP substrates in quiescent compared to activated PBLs. At these low dNTP concentrations, HIV-1 reverse transcriptase acts in a partially distributive manner. Increasing dNTP concentrations from the levels of quiescent PBLs to the levels of activated PBLs increases the processive action of the reverse transcriptase, which in turn stimulates rapid and efficient formation of full length DNA. Furthermore, hydroxyurea treatment of stimulated PBLs decreases the dNTP levels and the DNA synthesis rate to levels comparable to quiescent PBLs. Our data therefore indicate that low levels of dNTP may explain why HIV-1 DNA is synthesized slowly and inefficiently in quiescent PBLs and suggest that pharmacologic induction of low dNTP levels represents a therapeutic approach for inhibition of HIV-1 replication."

The explanation by Gao et al given for slow and inefficient HIV-1 viral DNA synthesis in quiescent PBLs may well be valid, given that viral DNA is synthesized completely in PBLs under conditions of sufficient replication/activation (Fauci, 1993, *Science*, 262:1011–1018.).

However, Gao et al fail to explain how HC (hydroxycarbamide or hydroxyurea] by means of its inhibitory action on ribonucleotide reductase, and the reduction of dNTP pools in activated lymphocytes, would constitute a potential use of HC in the treatment of patients with AIDS. At the concentration of 1 mM, HC partially reduces the various dNTP pools studied, see FIG. 4(a).

A comparison of table 1 (dNTP pools in quiescent and PHA stimulated PBLs) of Gao et al, and FIG. 4(a) (effect of HC on dNTP pools in PHA-stimulated PBLs) shows that the reduction of pools levels in table 1 is substantially greater than the HC-induced reduction over an equivalent 48 hour period. (See table 1).

In one accepts what Gao et al hypothesize that viral DNA synthesis in "resting" cells while show and inefficient eventually produces complete viral DNA capable of integration, it is difficult to understand how, under the conditions described, HC could have activity in AIDS patients. It is demonstrated in the present disclosure (FIG. 1) that quiescent cells in the presence of HC at nontoxic concentrations are incapable of preventing the production of infectious virions as measured by the HIV-1 p24 antigen in the supernatant after stimulation by PHA and IL-2.

An explanation of the HC-induced depletion of the dNTP pools which "significantly reduces the rate of HIV-1 DNA synthesis and inhibits the completion of viral DNA synthesis in PHA stimulated PBLs", see FIG. 4(b) of Gao et al, would by that HC at the concentration of 1 mM is cytotoxic for non-activated lymphocytes pretreated for 24 hours and activated by PHA and IL-2 for the following 48 hours in the presence of HC. Under such conditions, greater than 70% of the PBLs die due to the drug's toxicity.

Under the heading "Potential use of hydroxyurea in AIDS therapy", Gao et al state that "by depleting the cellular dNTP pool, hydroxyurea in expected to increase the therapeutic effect of nucleoside analogs 3'-azido-3'-deoxythymidine, dideoxyinosine, or dideoxycytosine, which act as competitors of cellular dNTP". If this were true, one would expect that, in the treatment of infected "resting" cells where dNTP pools are found at their lowest levels, nucleoside analogs would have a major effect. However, as shown in the present disclosure, (FIGS. 1 and 2) the treatment of "resting" cells infecting by HIV-1 for seven days and treated by AZT alone at 5 µM has only a slight effect on viral replication as measured by p24 antigen. Similarly, for ddI alone, at the same concentration, and under the same conditions, viral replication is only temporarily and partially inhibited, regaining the level of the infected control at day 25 (FIG. 1). It is not, therefore, in accepting the Gao et al explanation that one could have predicted an increase in the therapeutic effect in AIDS therapy by associating a nucleoside analog with HC, all the more so since the results in the present disclosure show that a surprising synergistic effect is observed for the association of HC and ddI, but not at all for HC and AZT.

The subject of the present invention is also a new composition for the treatment of a cell population in the presence of a retrovirus. Additionally, the invention includes a pharmaceutical composition intended, in particular, for the treatment and prevention of retroviral infections, especially those linked to HIV and AIDS wherein the composition contains a synergistic combination of hydroxycarbamide (HC) and a reverse transcriptase inhibitor, in particular a synergistic combination of a dideoxynucleoside except AZT and hydroxycarbamide, most preferably a synergistic combination of dideoxyinosine and hydroxycarbamide as active principle, in a pharmaceutically acceptable vehicle. The composition of the invention can also contain inert or pharmacodynamically active additives, carriers and/or excipients.

The pharmaceutical composition of the invention can take the form of a lypholized powder of the active substance, to be dissolved immediately before use in a physiological solution for the purpose of injection. The medicament can then be administered parenterally, for example intravenously, intraperitoneally, in the cerebrospinal fluid, and the like. For injection, the active principle is dissolved in a physiological solution until the desired concentration for administration is obtained.

The pharmaceutical composition according to the invention can also take a form which is suitable for oral administration. For example, suitable forms are tablets, hard gelatin capsules, dragées, powders and granules. The formation of such oral forms is well-known to those skilled in the art. Any of the known formulations are useful in preparing the instant oral pharmaceutical compositions.

As regards the dosage of the medicament according to the invention, it will be clear to the artisan that the doses to be administered are variable according to the treatment period, and frequency of administration, the host, and the nature and severity of the disease and that the dosages can be easily determined without any undue amount of experimentation.

The compositions of the invention are administered in substantially non-toxic dosage concentrations sufficient to insure the release of a sufficient dosage unit of the present synergistic combination into the patient to provide the desired inhibition of the spread of the retrovirus. The actual dosage administered will be determined by physical and physiological factors such as age, body weight, severity of condition, and/or clinical history of the patient. With these considerations in mind, the dosage of the instant synergistic combination for a particular subject can be readily determined by the physician. It might be noted that in extreme cases a dosage approaching the toxic level may be the acceptable treatment protocol.

For example, in the treatment of HIV-infected and AIDS patients, the composition can comprise from about 1 to 66 mg/Kg/day of ddI and from about greater than 5 mg/Kg/day to about 20 mg/Kg/day of HC.

The invention also covers the use of hydroxycarbamide (HC) and dideoxyinosine in combination with other medical compositions intended for the treatment of retroviral infections and tumors. Immunostimulants and immunomodulators such as for example cytokines, including IL-2, IL-12 and interferon molecules can be used in combination with the present invention.

A preferred range for in vitro administration of the compositions of the present invention includes hydroxycarbamide in a concentration greater than 0.05 mM and less than or equal to 0.25 mM in combination with a dideoxynucleoside except AZT such as ddI at concentrations which are generally known and used in the art. A preferred embodiment of the present invention utilizes HC at 0.15 mM and the dideoxynucleoside such as ddI in a range of between about 0.01 µM to about 100 µM, preferably between about 2.5 µM to about 25 µM, most preferably from about 5 µM to about 10 µM.

All of the references cited hereinabove are expressly incorporated herein, in toto, by reference thereto.

The invention has been described with reference to specific and preferred embodiments. It will be recognized by those skilled in the art that numerous changes and substitutions may be made without departing from the spirit and scope of the invention.

We claim:

1. A method of treating an HIV infected human comprising administering to said human a dosage of hydroxycarbamide (HC) to yield an in vivo blood plasma concentration of about 0.15 mM and a dosage of 2', 3'-dideoxyinosine (ddI) to produce an in vivo blood plasma concentration in the range of about 5–10 μM.

2. A method of treating an HIV infected human comprising administering to said human a dosage of hydroxycarbamide (HC) to yield an in vivo blood plasma concentration of about 0.15 mM and a dosage of 2', 3'-dideoxyinosine (ddI) to produce an in vivo blood plasma concentration of about 5 μM.

3. A method of treating an HIV infected human comprising administering to said human a dosage of hydroxycarbamide (HC) to yield an in vivo blood plasma concentration of about 0.15 mM and a dosage of 2', 3'-dideoxyinosine (ddI) to produce an in vivo blood plasma concentration of about 10 μM.

* * * * *